(12) United States Patent
Riedel et al.

(10) Patent No.: US 10,309,817 B2
(45) Date of Patent: Jun. 4, 2019

(54) METHOD AND ULTRASOUND FLOW MEASUREMENT UNIT FOR THE DETERMINATION OF THE $CO_2$ EMISSION FACTOR IN FLARE GAS PLANTS

(71) Applicant: SICK Engineering GmbH, Ottendorf-Okrilla (DE)

(72) Inventors: Ekkehard Riedel, Ottendorf-Okrilla (DE); Alexander Nerowski, Ottendorf-Okrilla (DE)

(73) Assignee: SICK ENGINEERING GMBH, Ottendorf-Okrilla (DE)

( * ) Notice: Subject to any disclaimer, the term of this patent is extended or adjusted under 35 U.S.C. 154(b) by 298 days.

(21) Appl. No.: 14/965,966

(22) Filed: Dec. 11, 2015

(65) Prior Publication Data

US 2016/0169727 A1 Jun. 16, 2016

(51) Int. Cl.
*G01F 15/04* (2006.01)
*G01N 29/024* (2006.01)
(Continued)

(52) U.S. Cl.
CPC .............. *G01F 15/04* (2013.01); *G01F 1/662* (2013.01); *G01N 29/024* (2013.01);
(Continued)

(58) Field of Classification Search
CPC ................. G01F 15/04; G01F 1/662
(Continued)

(56) References Cited

U.S. PATENT DOCUMENTS 6,216,091 B1 4/2001 Hammond
7,752,884 B2 7/2010 Huang
(Continued)

FOREIGN PATENT DOCUMENTS

DE 202006021163 U1 9/2013
EP 1063525 A2 12/2000
(Continued)

OTHER PUBLICATIONS

North Sea Flow Measurement Workshop, NEL Technology for Life; Oct. 26-29, 2010; Scotland, UK.
(Continued)

*Primary Examiner* — Ricky Ngon
(74) *Attorney, Agent, or Firm* — Nath, Goldberg & Meyer; Jerald L. Meyer

(57) ABSTRACT

The invention relates to an improved and simpler method and to an apparatus for the determination of the $CO_2$ emission factor in flare gas plants comprising the steps:
a) measuring the speed of sound in the flare gas;
b) detecting known proportions of $N_2$, $CO_2$ and $H_2O$;
c1) calculating a maximum speed of sound of the flare gas under the assumption that the hydrocarbon proportion of the flare gas only consists of alkanes having a chain length i;
c2) calculating a minimal speed of sound of the flare gas under the assumption that the hydrocarbon proportion of the flare gas only consists of alkanes having a chain length i+1;
c3) varying the chain length i for so long until the measured speed of sound lies between the calculated minimal speed of sound and the calculated maximum speed of sound;
d) varying the proportions of the alkanes having the chain length i and the chain length i+1 determined in step c) for so long until the speed of sound calculated with these proportions lies within a predefined difference from the measured speed of sound;
e) calculating the equivalent chain length; and
f) calculating the emission factor.

7 Claims, 2 Drawing Sheets

Figure 1:
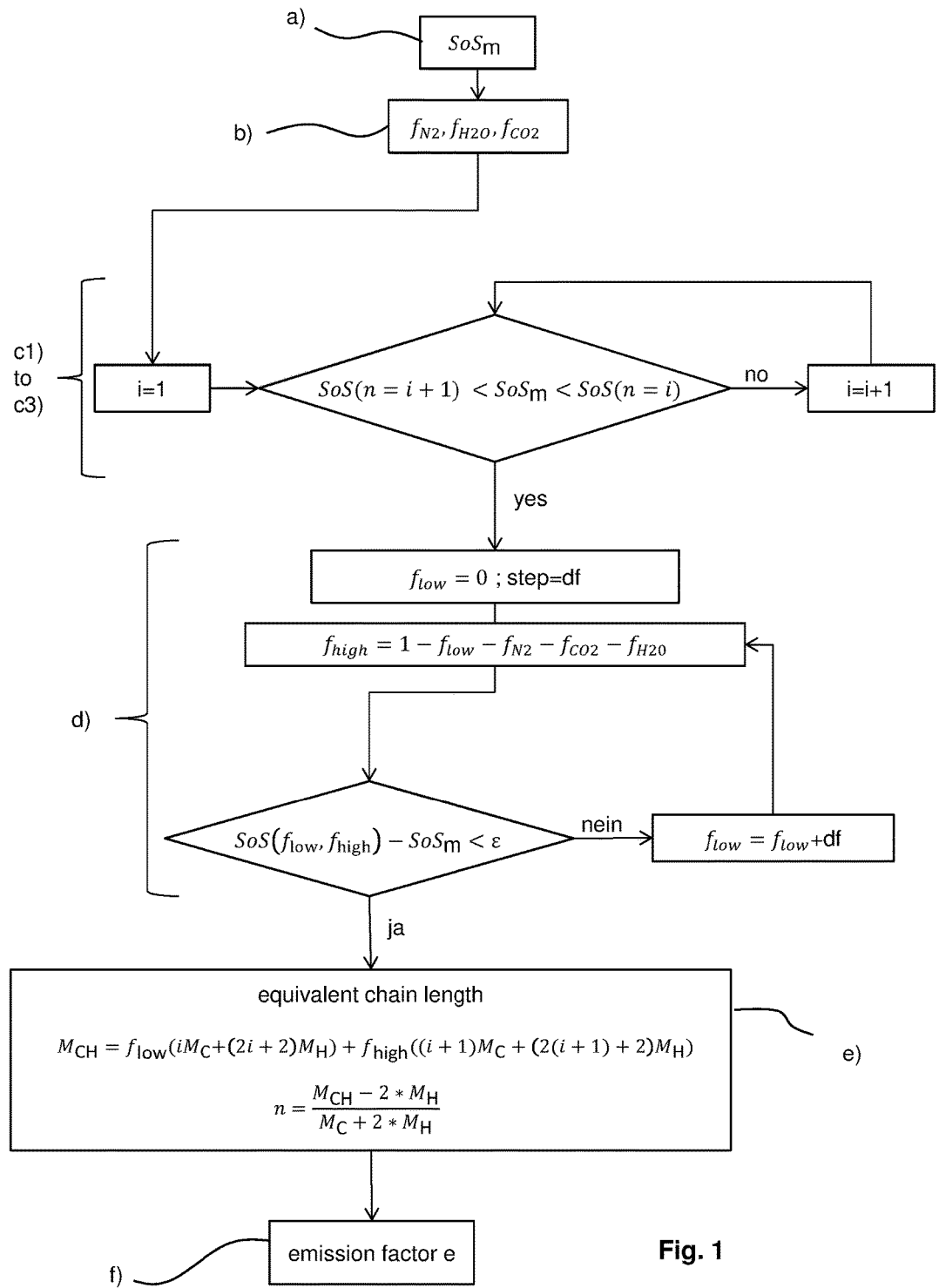

(51) Int. Cl.
*G01F 1/66* (2006.01)
*G01N 33/00* (2006.01)

(52) U.S. Cl.
CPC . *G01N 33/004* (2013.01); *G01N 2291/02836* (2013.01); *Y02A 50/244* (2018.01)

(58) Field of Classification Search
USPC .......................................................... 702/24
See application file for complete search history.

(56) References Cited

U.S. PATENT DOCUMENTS

| 2003/0082821 | A1 | 5/2003 | Lanier et al. |
| 2008/0134755 | A1 | 6/2008 | Huang |
| 2014/0336953 | A1* | 11/2014 | Johnson ............... G01N 21/538 702/24 |

FOREIGN PATENT DOCUMENTS

| EP | 2330347 A1 | 8/2011 |
| RU | 2226263 C2 | 10/2003 |

OTHER PUBLICATIONS

European Search Report dated Apr. 30, 2015 corresponding to European application No. 14197704.1-1553.
Search report dated Jan. 25, 2017 for corresponding application 2015152604.
Hallander, Anders et al. "A Cost-Effective Approach on CO2 Emission Factor Estimation for Flare Ultrasonic Metering Systems", International North Sea Flow Measurement Workshop, Oct. 26-29, 2010, pp. 175-191.
Matson, Jed et al. "Ultrasonic Flare Gas Flow Meter Techniques for Extremes of High and Low Velocity Measurement and Experience with High C02 Concentration", International North Sea Flow Measurement Workshop, Oct. 26-29, 2010, pp. 135-140.

* cited by examiner

METHOD AND ULTRASOUND FLOW MEASUREMENT UNIT FOR THE DETERMINATION OF THE $CO_2$ EMISSION FACTOR IN FLARE GAS PLANTS

The invention relates to a method for the determination of the $CO_2$ emission factor in flare gas plants as well as to an ultrasound flow measurement unit with which this method can be carried out.

Taxes have to be paid on $CO_2$ emissions due to new EU directives (e.g. Directive 2003/87/EC of the European Parliament and of the Council of Feb. 26, 2004, announced under file reference K(2004) 130 and published in the official journal of the European Union L 59/1 to L59/74) and in some cases also due to national directives (e.g. in Norway). Since the tax burden increases the less accurately the $CO_2$ emissions are known, it is necessary to monitor the $CO_2$ emissions accumulated over time continuously and as accurately as possible. Solutions are in particular being sought for flare gas plants since a measurement of the $CO_2$ arising on the combustion of the gas (also called "flare gas") is very difficult since the combustion takes place with a naked flame.

The $CO_2$ content of a gas can be measured using different methods. They include inter alia Fourier transform infrared (FTIR) spectroscopy, gas chromatography and flame ionization detection (FID).

FTIR spectroscopy is an optical process in which infrared light (wavelengths of 800 nm to 1 m) is shone into the gas and the absorption is measured. The wavelength(s) at which absorption occurs is/are molecule-specific and the intensity of the absorption correlates with the molar portion of the molecule in the total gas. The process only works with molecules which have an IR-active bonding, which, however, applies to $CO_2$.

In flare gas applications, two application sites are conceivable with an FTIR unit, namely before the flame and after the flame. Since, however, there is the problem of high contamination in flare gas pipelines, optical solutions before the flame are not practical because the transparent parts directly in contact with the gas are no longer light-permeable after a certain operating time. Measuring the $CO_2$ emission after the flame is associated with substantial difficulties since the burned gas diffuses absolutely freely into the atmosphere.

In gas chromatography, the individual components of a gas mixture are separated by their boiling points and their polarities and are individually measured. It is disadvantageous with this that gas chromatography is a very inactive process so that a continuous monitoring is not possible. In addition, gas chromatographs are very expensive in purchase.

In flame ionization detection (FID), the gas to be analyzed is burned at a hydrogen flame. The ions which arise are sucked off by an electrode with the aid of acceleration voltage so that a current can be measured which is proportional to the total content of hydrocarbons of the gas.

An FID can only detect hydrocarbons so that the unit would have to be positioned in front of the flame since the hydrocarbons are decomposed after the flame. An FID unit is, however, not suitable for regions subject to explosion hazards due to its hydrogen flame and can therefore not be considered for measurements in front of the flare flame where the methane portion of the gas is often around 90%. A measurement after the flame cannot be considered since hydrocarbons are no longer contained in the gas after the combustion and the unit is not sensitive to other gases.

It is common to all these three solutions that an additional unit has to be installed at the gas line which measures the volume flow to obtain the $CO_2$ emissions accumulated over time.

A further prior art is known from Froysa et al. Conference Volume "28th International North Sea Flow Measurement Workshop 2010", ISBN: 978-1-61782-294-0, Publ: Energy Institute, POD Publ: Curran Associates, Inc. (April 2011), page 145, "A Cost-Effective Approach on $CO_2$ Emission Factor Estimation for Flare Ultrasonic Metering Systems" by Jeff Gibson, Richard Paton, Pal Jagho, Kjell-Eivind Froysa, Anders Hallanger, Endre Jacobsen and Anders Lovoll Johansen). It is described here how the $CO_2$ emissions arising on a combustion can be determined from specific input parameters and from a flow determined by a flow measuring unit, as will be briefly described in the following.

The total mass $m_{CO2}$ of the emitted $CO_2$ is composed of the hydrocarbons contained in the gas during the combustion and the $CO_2$ already present in the gas.

$$m_{CO2}(\text{total}) = m_{CO2}(\text{from combustion}) + m0_{CO2}(\text{already present in the gas}) \tag{1}$$

According to the guidelines for monitoring and reporting greenhouse gas emissions in accordance with the aforesaid directive 2003/87/EC, an emission factor e and an oxidation factor $\Omega$ are defined. These factors represent a measure for how much $CO_2$ ($m_{CO2}$) arises on the combustion of a quantity $m_{Flare}$ of the gas, wherein the dimensionless oxidation factor $\Omega$ states which proportion of the hydrocarbons contained in the flare gas is burned. The value 1 corresponds to a full combustion of the hydrocarbons to $CO_2$. $\Omega$ is given with sufficient accuracy as 0.98 by the plant operators.

$$m_{CO2}(\text{combustion}) = \text{emission factor } e * m_{Flare} * \Omega \tag{2}$$

$$\Rightarrow e * \Omega = \frac{m_{CO2}}{m_{Flare}} \tag{3}$$

This mass ratio can also be expressed in molar terms $$\Rightarrow e * \Omega = \frac{m_{CO2}}{m_{Flare}} = \frac{M_{CO2}}{M_{Flare}} * \sum_{i=1}^{N} f_i * n_i \tag{4}$$

where $f_i$ is the proportion of the ith carbon compound and $n_i$ is the number of carbons in the ith carbon compound and is summed over all carbon compounds occurring in the flare gas.

The carbon compounds occurring in the flame gas are unknown in principle. It has, however, been found that the error remains acceptable if it is assumed that they only occur as alkanes of different chain lengths, with the chain length normally not being larger than 6. The molar mass $M_{Flare}$ and thus the emission factor e can then be calculated using a so-called equivalent chain length n and the proportion of the hydrocarbons $f_{CH}$. It applies to the equivalent chain length:

$$n = \frac{\sum_{i=1}^{N} \text{if } C_i H_{2i+2}}{f_{CH}} \tag{5}$$

and using this equivalent chain length to the molar mass of the hydrocarbons (alkanes):

$$M_{CH} = nM_C + (2n+2)M_H \quad (6)$$

The molar mass of the flare gas can be calculated with this, with the flare gas also having portions of nitrogen, carbon dioxide and water in addition to the hydrocarbons:

$$M_{Flare} = f_{CH}M_{CH} + f_{N2}M_{N2} + f_{H2O}M_{H2O} + f_{CO2}M_{CO2} \quad (7)$$

The different proportions $f_{N2}$, $f_{H2O}$, $f_{CO2}$ and $f_{CH} = 1 - (f_{N2} + f_{H2O} + f_{CO2})$ are acquired from empirical values in the operation of a plan and are input as estimated values by the user as parameters before the calculation. It thus results for the emission $e*\Omega$ arising due to the combustion:

$$e*\Omega = \frac{M_{CO2}}{M_{Flare}} * (nf_{CH}) \quad (8)$$

It thus results overall for the total mass flow $\dot{m}$, that is for the total $CO_2$ emission (quantity of $CO_2$) per time:

$$\dot{m}_{CO2}(\text{total}) = \dot{m}_{CO2}(\text{combustion}) + \dot{m}0_{CO2}(\text{already in the gas}) \quad (10)$$

$$= \dot{m}_{Flare} * e * \Omega + \dot{m}_{Flare} * f_{CO2}$$

$$= \varrho * \dot{Q} * e * \Omega + \varrho * \dot{Q} * f_{CO2}$$

$$= \varrho * \dot{Q} * (e * \Omega + f_{CO2})$$

where $\dot{Q}$ is the volume flow and $\varrho$ is the density of the gas. The density is estimated using known algorithms by a measured speed of sound. The volume flow is measured using an ultrasound measurement unit. The proportion $f_{CO2}$ in the $CO_2$ already present in the gas before the combustion is known.

The $CO_2$ emission can then be determined with this, with the speed of sound and the volume flow forming the only measurement parameters.

The invention takes up this principle, that is the determination of the $CO_2$ emission over a measured volume flow in connection with the idea of the equivalent chain length for calculating the emission factor. In this respect, however, a new solution will be shown how the gas composition can be determined better in order to allow a more reliable measure from this for the continuous monitoring of the $CO_2$ emission at a flare gas line without an additional unit having to be installed.

This object is satisfied by a method having the features of claim 1 and by an apparatus in accordance with claim 8.

The method in accordance with the invention for the determination of the $CO_2$ emission factor in flare gas plants comprises the steps:

a) measuring the speed of sound in the flare gas;
b) detecting known proportions of $N_2$, $CO_2$ and $H_2O$;
c1) calculating a maximum speed of sound of the flare gas under the assumption that the hydrocarbon proportion of the flare gas only consists of alkanes having a chain length i;
c2) calculating a minimal speed of sound as under the assumption that the hydrocarbon proportion of the flare gas only consists of alkanes having a chain length i+1;
c3) varying the chain length i for so long until the measured speed of sound lies between the calculated minimal speed of sound and the calculated maximum speed of sound;
d) varying the proportions of the alkanes having the chain length i and the chain length i+1 determined in step c) for so long until the speed of sound calculated with these proportions lies within a predefined difference from the measured speed of sound;
e) calculating the equivalent chain length; and
f) calculating the emission factor.

This new method comprises the essential key idea that the hydrocarbons of the flare gas for the calculation of the emission factor are so-to-say replaced with only a "matching" pair of alkanes having adjacent chain lengths, that is having the chain lengths i and i+1.

The "matching" pair of alkanes is found by a first variation, preferably iteratively, in that the respective speed of sound of the theoretical flare gas is calculated whose hydrocarbons respectively only have the one or only have the other alkane and the calculated speed of sound is compared with the actually measured speed of sound. If the measured speed of sound lies between the two calculated ones, the "matching pair" of alkanes is found. A first rough approximation of the composition of the flare gas is thus obtained.

This procedure in accordance with the invention simplifies the further numerical determination of the gas composition since the number of degrees of variation for the proportions of hydrocarbons is reduced from 6 as in the prior art of Fröysa et al to two. This simplification for the conversion of hydrocarbon mixtures to a mixture of only two different alkanes, however, has an uncertainty with respect to the consideration of the two hydrogen atoms at the start and at the end of the molecule chains. This uncertainty has, however, been found to be acceptable with respect to the total uncertainty of the method.

In a second variation of the proportions of the two alkanes found in this manner, the proportions are varied stepwise, preferably starting from a starting state in which the one proportion is zero and the other proportion is at a maximum, until the speed of sound calculated using the respective proportions is close enough (within an abort criterion) to the measured speed of sound.

If the proportions have been found in this manner, the equivalent chain length and from this the emission factor can be calculated. The $CO_2$ emission can then be calculated via the gas flow measured using a flow measurement unit and the oxidation factor.

The method in accordance with the invention first delivers more accurate results than the methods of the prior art and second is simpler to carry out. In principle it only consists of two phases.

In the first phase, the index i is varied in a preferably iterative algorithm and the speed of sound is calculated in each iteration step for the mixture only having hydrocarbon molecules of two chain lengths. The algorithm according to GERG-2004 XT08 is preferably used for the calculation (see also "The GERG-2004 Wide-Range Equation of State for Natural Gases and Other Mixtures" by O. Kunz, R. Klimeck, W. Wagner, M. Jaeschke in GERG TECHNICAL MONOGRAPH 15 (2007), VDI Verlag GmbH, Düsseldorf 2007, Reprinted from Fortschritt-Berichte VDI, Series 6 No. 557 (2007), ISBN 978-3-18-355706-6). Alternatively, other methods can also be used e.g. AGA report 10 (AGA Report No. 10, Speed of Sound in Natural Gas and Other Related Hydrocarbon Gases, January, 2003) or GSSSD MR 113-03 (Hydrocarbon Gas). The iteration loop is run through for so long until the measured speed of sound of the ultrasound gas counter lies within the theoretical speeds of sound of the flare gases which only have "pure" alkanes having a single chain length of 1 or i+1.

In the second phase, the mixing ratio of the two alkanes having chain lengths i and i+1 is determined.

A suitable apparatus for the implementation of the method is formed in accordance with the invention by an ultrasound flow measurement unit having an input unit for inputting the known proportions of $N_2$, $CO_2$ and $H_2O$, having ultrasonic converters for the transmission and reception of ultrasonic signals and having an evaluation unit which is configured to determine a speed of sound from the ultrasonic signals and to carry out the steps a) to h) of the method and to determine the gas flow via the measured flow speed, wherein the flow speed can be determined from the time of flight difference of two ultrasonic signals which have one component with the flow, on the one hand, and which have one component against the flow, on the other hand.

Such an apparatus can therefore not only carry out the method in accordance with the invention, but can also perform the measurement of the speed of sound of the flare gas.

Finally, the $CO_2$ emission can be calculated more accurately and can be output continuously using the method and apparatus in accordance with the invention using the gas flow and the emission factor.

Figure 2:
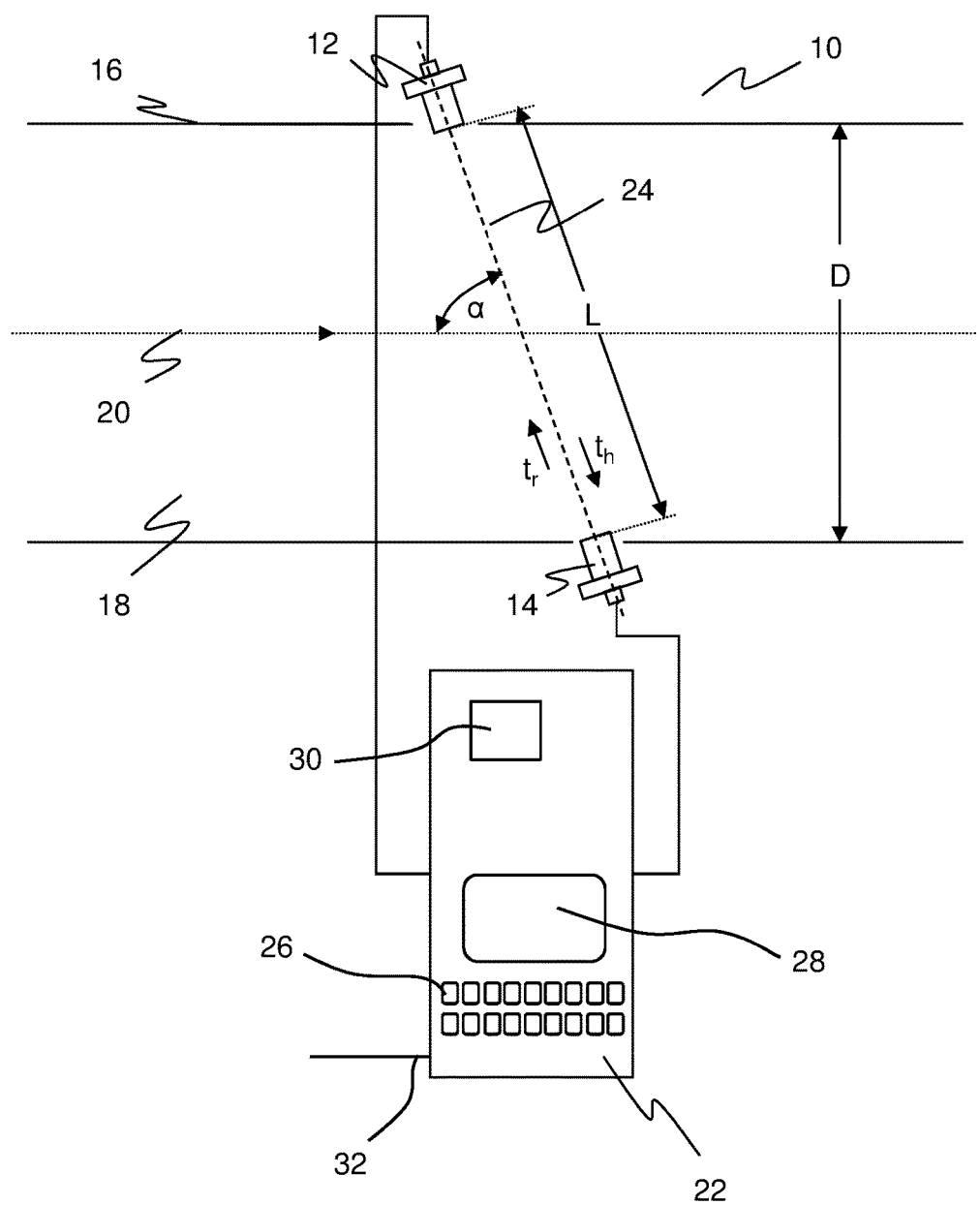

The invention will be explained in detail in the following with reference to an embodiment and to the drawing. There are shown in the drawing:

FIG. 1 an exemplary flowchart of the method in accordance with the invention; and FIG. 2 a schematic representation of an ultrasound flow measurement unit in accordance with the invention.

The method in accordance with the invention will first be described by way of example.

FIG. 1 shows a flowchart. In a first step a), the speed of sound $SoS_m$ in the flare gas is measured.

A flare gas is typically composed of different gases of which the hydrocarbons (CH) are converted into $CO_2$ in the combustion. The other components which are not converted to $CO_2$ in a combustion are nitrogen ($N_2$), water ($H_2O$) and carbon dioxide ($CO_2$).

The proportions of the inert components are known as a rule and are detected in a second step b) e.g. in that they are manually input.

In contrast, the proportions of the different hydrocarbons are unknown; however, they decisively influence the $CO_2$ emission on the combustion of the flare gas by their combustion to $CO_2$.

To obtain a better estimate here, the initially described principle which is described by Fröysa et al. is applied according to which it is assumed for the hydrocarbons that they are only present as alkanes. The invention now goes even further and assumes that only two types of alkane occur, and indeed those which have adjacent chain lengths, that is the one hydrocarbon proportion is an alkane having the chain length i with a proportional factor of $f_{low}$ and the other hydrocarbon proportion has the chin length i+1 and a proportional factor of $f_{high}$. The molar mass of the hydrocarbon in the flare gas is then $$M_{CH} = f_{low}(iM_C + (2i+2)M_H) + f_{high}((i+1)M_C + (2(i+1)+2)M_H) \quad (11)$$

In the next three steps c1) to c3), the chain length i is then determined. This is done in this embodiment by iteration, starting with i=1.

In the first part step c1), a maximum speed of sound $SoS(f_{high}=0)$ of the flare gas is calculated. It is assumed in this respect that only alkanes having a chain length i occur, that is $f_{high}=0$ and $f_{low}=1-(f_{CO2}+f_{H2O}+f_{N2})$. The calculation of the speed of sound $SoS(f_{high}=0)$ takes place in accordance with the algorithm GERG-2004 XT08.

In the second part step c2), a minimal speed of sound $SoS(f_{low}=0)$ of the flare gas is calculated. It is assumed in this respect that only alkanes having a chain length i+1 occur, that is $f_{low}=0$ and $f_{high}=1-(f_{CO2}+f_{H2O}+f_{N2})$.

Finally, a check is made in the third part step c) whether the measured speed of sound lies between the two calculated speeds.

$$SoS(f_{low}=0; n=i+1) < SoS_m < SoS(f_{high}=0; n=i) \quad (12)$$

The part steps c1) to c3) are each run through iteratively with an increase of the chain length i by 1 for so longer until the measured speed of sound lies between the two calculated speeds. The "matching pair" of alkanes is then found.

In the next step d), the proportions, that is $f_{low}$ and $f_{high}$, of the two alkanes are determined. This is done in that and $f_{low}$ and $f_{high}$ are again varied (with $1=f_{low}+f_{high}+f_{CO2}+f_{H2O}+f_{N2}$ applying as above) in an iteration starting from $f_{low}=0$ (or alternatively from $f_{high}=0$) in fixed steps of the magnitude df and the speed of sound SoS is calculated in each iteration step and is compared with the measured $SoS_m$. If the calculated and the measured speeds of sound are less than a predefined difference ε apart from one another (abort criterion), the sought $f_{low}$ and $f_{high}$ are found.

The molar mass of the alkanes can be calculated in accordance with equation (11) using the proportional factors f thus found. The equivalent chain length is formed in a step e) using equation (13). It amounts to:

$$n = \frac{M_{CH} - 2 * M_H}{M_C + 2 * M_H} \quad (13)$$

The molar masses of hydrogen and carbon obtained in equation (13) are known and can be taken from literature values.

In a final step f), the emission factor can be calculated using the effective chain length with equation (8) in conjunction with (6) and (7). If the gas flow is known, the $CO_2$ emission can be calculated using the emission factor.

A flow measurement unit 10 in accordance with the invention will be described in the following with which the method in accordance with the invention can be carried out and the $CO_2$ emission can be calculated from a measured gas flow and the emission factor e.

The flow measurement unit 10 in accordance with the invention works in accordance with the principle of a flow measurement by means of ultrasound. This known measuring principle is shown in FIG. 2. The flow measurement unit 10 comprises two ultrasonic transducers 12, 14 which are arranged at an angle in the wall of a pipeline 16 in which a fluid 18 flows in the direction of the arrow 20. The ultrasonic transducers 12, 14 work, controlled by a control and evaluation unit 22, alternately as transmitters and receivers. The ultrasonic signals transported on a measured path 24 by the fluid 18 are accelerated in the direction of flow and are braked against the direction of flow. The respective received signals are supplied to the control and evaluation unit 22 and are digitally evaluated via circuit elements such as amplifiers and A/D converters. The resulting time of flight difference in accordance with $$v = \frac{L}{(2\cos\alpha)\left(\frac{1}{t_h} - \frac{1}{t_r}\right)}$$

is offset from the sought flow speed or in accordance with $$\dot{Q}=v\tfrac{1}{4}D^2\pi \quad (15)$$

from the volume flow in which the geometrical relationships are described as in FIG. 2 by the following variables:
v: flow speed of the fluid in the line;
L: length of the measurement path between the two ultrasonic transducers;
α: angle at which the ultrasonic transducers transmit and receive
Q: volume flow
D: diameter of the line;
th: time of flight of the ultrasound with the flow; and
tr: time of flight of the ultrasound against the flow It is understood that the speed of sound of the flowing gas can also be determined using this arrangement in accordance with $$SoS = \frac{2L}{(t_h + t_r)}.$$

The evaluation unit 22 comprises input means 26 for inputting the required parameters such as the proportional factors $f_{N2}$, $f_{H2O}$, $f_{CO2}$, a display unit 28 for displaying inter alia determined or measured results such as the speed of sound SoS and the flow, whether the volume flow $\dot{Q}$ or the mass flow $\dot{m}$, and an emission factor calculation unit 30 in which the method in accordance with the invention runs. Such an apparatus 10 can not only carry out the method in accordance with the invention, but can also perform the measurement of the speed of sound of the flare gas.

Finally, the $CO_2$ emission can be calculated in accordance with equation (10) using the method in accordance with the invention and the apparatus using the gas flow and the emission factor and can be continuously output e.g. at an output 32.

In a similar manner to the above-described method, an unknown nitrogen proportion $f_{N2}$, which may occur in practice, could be determined with a known equivalent chain length n. Such a method would then comprise the following steps:
a) measuring the speed of sound in the flare gas;
b) detecting known proportions of $CO_2$ and $H_2O$;
c) calculating the hydrocarbon proportions from the equivalent chain length;
d) varying the nitrogen proportion for so long until the speed of sound calculated with this proportion lies within a predefined difference from the measured speed of sound; and
e) calculating the emission factor.

The invention claimed is:

1. A method for the determination of the $CO_2$ emission factor in flare gas plants comprising the steps of:
a) using an ultrasound flow measurement unit having an ultrasonic conversion capability for converting transmission and reception of ultrasonic signals and having an evaluation unit configured to determine a speed of sound from the ultrasonic signals to measure the speed of sound ($SoS_m$) in the flare gas and to determine a gas flow via the measured flow speed from the time of flight difference of two ultrasonic signals which have respective components with and against the gas flow, wherein the ultrasound flow measurement unit comprises first and second ultrasonic transducers for respectively generating and receiving the two ultrasonic signals, the first and second ultrasonic transducers being arranged at an angle in a wall of a pipeline through which the flare gas flows, and wherein the two ultrasonic signals are accelerated by the flare gas in a direction of the gas flow and are decelerated by the flare gas in a direction opposite the direction of the gas flow;
b) detecting known proportions ($f_{N2}$, $f_{H2O}$, $f_{CO2}$) of $N_2$, $CO_2$ and $H_2O$;
c1) calculating a maximum speed of sound ($SoS(f_{high}=0)$) of the flare gas as measured by the ultrasound flow measurement unit under the assumption that the hydrocarbon proportion ($f_{CH}$) of the flare gas only consists of alkanes having a chain length i;
c2) calculating a minimal speed of sound ($SoS(f_{low}=0)$) of the flare gas under the assumption that the hydrocarbon proportion ($f_{CH}$) of the flare gas only consists of alkanes having a chain length i+1
c3) varying the chain length i for so long until the measured speed of sound ($SoS_m$) lies between the calculated minimal speed of sound and the calculated maximum speed of sound;
d) varying the proportions ($f_{low}$ and $f_{high}$) of the alkanes having the chain length i and the chain length i+1 determined in steps c1) to c3) for so long until the speed of sound (SoS) calculated with these proportions ($f_{low}$ and $f_{high}$) lies within a predefined difference from the measured speed of sound ($SoS_m$);
e) calculating an equivalent chain length; and
f) calculating an emission factor.

2. The method in accordance with claim 1, wherein the chain length is determined in iterative steps starting at i=1 in step e).

3. The method in accordance with claim 1, wherein the proportions are determined in iterative steps in step d).

4. The method in accordance with claim 1, wherein the step of calculating the speed of sound takes place in accordance with the GERG-2004 XT08 algorithm.

5. The method in accordance with claim 1, further comprising the steps of: determining a gas flow using an ultrasound flow measurement unit and calculating the $CO_2$ emission using the flow and the emission factor.

6. The method in accordance with claim 5, further comprising the step of using the measured speed of sound for the calculation of the density of the flare gas.

7. An ultrasound flow measurement unit for the carrying out of a method in accordance with claim 1, having an input unit for inputting the proportions ($f_{N2}$, $f_{H2O}$, $f_{CO2}$) of $N_2$, $CO_2$ and $H_2O$, having ultrasonic transducers for transmitting and receiving ultrasonic signals, having an evaluation unit which is configured to measure a speed of sound ($SoS_m$) and to carry out the steps a) to h) in accordance with claim 1, and to determine a gas flow via the measured flow speed, wherein the flow speed can be determined from the time of flight difference of two ultrasonic signals which have one component with the flow, on the one hand, and one component against the flow, on the other hand.

* * * * *